(12) United States Patent
Töllner et al.

(10) Patent No.: US 6,595,991 B2
(45) Date of Patent: Jul. 22, 2003

(54) ABLATION CATHETER FOR THE GENERATION OF LINEAR LESIONS IN THE MYOCARDIUM

(75) Inventors: Thomas Töllner, Berlin (DE); Michelle Maxfield, Berlin (DE); Jan-Helge Richter, Berlin (DE)

(73) Assignee: Biotronik Mess- und Therapiegerate GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/792,029

(22) Filed: Feb. 26, 2001

(65) Prior Publication Data

US 2001/0031942 A1 Oct. 18, 2001

(30) Foreign Application Priority Data

Feb. 25, 2000 (DE) .......................... 100 08 918

(51) Int. Cl.[7] .............................. A61B 18/18
(52) U.S. Cl. ....................................... 606/41
(58) Field of Search ................ 606/41, 45, 46, 606/47, 48, 49, 50; 607/98, 99, 115, 122; 600/374

(56) References Cited

U.S. PATENT DOCUMENTS

| 5,284,138 | A |   | 2/1994  | Kujawski et al. |
| 5,398,683 | A |   | 3/1995  | Edwards et al. |
| 5,637,090 | A |   | 6/1997  | McGee et al. |
| 5,685,878 | A |   | 11/1997 | Falwell et al. |
| 5,730,127 | A |   | 3/1998  | Avitall |
| 5,849,028 | A |   | 12/1998 | Chen |
| 5,897,552 | A | * | 4/1999  | Edwards et al. ............ 600/549 |
| 5,967,976 | A | * | 10/1999 | Larsen et al. ............... 600/374 |
| 6,002,956 | A | * | 12/1999 | Schaer ........................ 600/381 |
| 6,391,024 | B1| * | 5/2002  | Sun et al. ..................... 606/34 |

FOREIGN PATENT DOCUMENTS

| DE | 197 21 362 A1 | 10/1998 |
| DE | 197 50 850 C1 | 7/1999 |
| EP | 0 765 178 B1  | 11/1999 |
| WO | WO 99/04696 A1| 2/1999 |

* cited by examiner

*Primary Examiner*—Linda C. M. Dvorak
*Assistant Examiner*—R. Kearney
(74) *Attorney, Agent, or Firm*—Browdy and Neimark, P.L.L.C.

(57) ABSTRACT

An ablation catheter for the generation of linear lesions in the myocardium is provided with an elongated catheter body and a linear, substantially cylindrical ablation electrode on the distal end of the catheter body. At least one sensing electrode is disposed in the ablation electrode, insulated therefrom and embedded in the jacket thereof.

13 Claims, 6 Drawing Sheets

ABLATION CATHETER FOR THE GENERATION OF LINEAR LESIONS IN THE MYOCARDIUM

BACKGROUND OF THE INVENTION

1. Field of the Invention

The invention relates to an ablation catheter for the generation of linear lesions in the myocardium, comprising an elongated catheter body, which has a proximal and a distal end; and a linear, substantially cylindrical ablation electrode on the distal end of the catheter body.

2. Background Art

As for the background of the invention, it can be said that catheter ablation is a frequently used therapy for the treatment of certain arrhythmias. A lesion—a sort of tissue removal or scar—is generated at a certain position in the myocardium by the aid of the ablation electrode of the catheter, interrupting the defective electrical stimulus conduction that is responsible for the arrhythmias. Linear lesions are in particular produced for the treatment of atrial flutter or fibrillation.

Applying energy to the cardiac tissue via the ablation electrode takes place either by high voltage direct current (DC) or by electromagnetic radiation in the radio frequency range—which has recently become the preferred method, owing to DC problems. A fundamental requirement in ablation therapy resides in the precise placement of the ablation electrode within the heart.

Conventional ablation catheters of a first basic design comprise unipolar ablation electrodes of point action so that they have to be displaced frequently for individual ablation steps if linear i.e., elongated, lesions are to be generated. This is time-consuming and comparatively inaccurate because of the local inaccuracy of the position of the ablation electrode within the heart. Another design which has been improved in this regard resides in ablation catheters having multipolar electrodes of point action, the individual poles of which are to be triggered sequentially by an especially suitable ablation control system.

U.S. Pat. No. 5,676,693 teaches an ablation catheter for the generation of linear lesions, which produces a longitudinal, quasi liquid electrode by means of conductive fluid emerging from the catheter and several electrodes placed therein.

U.S. Pat. No. 5,800,428 teaches an ablation catheter for the generation of linear lesions, which has a thin, elongated wire-type ablation electrode on the distal end. In a special design, several combined wires are provided as ablation electrodes on the distal end, spread up two- or three-dimensionally. In this case, the electrode wires may be electrically insulated from each other.

Finally, U.S. Pat. No. 5,676,662 teaches an ablation catheter for the generation of linear lesions, in which the ablation electrode consists of a spirally coiled conductor with spaced turns; this conductor is partially embedded in the catheter body and covered also from outside by an insulating layer which is recessed along a longitudinally parallel strip for the outside of the spirally coiled conductors to lie open. In this area they constitute the ablatively effective, linear zone of the electrode.

In this ablation catheter it is provided to make part of the turns of the ablation electrode separately triggerable so that the separated conductor pieces are suitable to serve as a scanning electrode for the detection of electrocardiologic signals before and after the actual ablation process—for the so-called mapping. As a result of this configuration, various sections of the spiral electrode section can detect or scan various sections of the myocardium without displacement of the spiral electrode.

The known ablation electrodes have in common that, owing to the limited or non-existent possibilities of scanning electrocardiogic signals, the accuracy of positioning leaves much to be desired.

SUMMARY OF THE INVENTION

It is an object of the invention to further develop an ablation catheter of the generic type such that the ablation electrode has improved positioning properties.

This object is attained by at least one sensing electrode being embedded in, and insulated from, the jacket of the ablation electrode.

As a result of this combination of ablation and sensing electrode, it is possible to produce a longitudinal lesion in a single ablation job by the linear ablation electrode. The substantial disadvantage which resides in that these longitudinal electrodes usually are hard to position because they do not offer sufficient perceptivity lengthwise is suppressed by the additional sensing electrode. While, in the case of sensing by a long electrode, the electric excitation front when spreading through the myocardium integrates towards zero in terms of signal implementation along the long electrode, the sensing electrode, which is embedded in the ablation electrode, can be made very short and thus highly perceptive and locally specific.

Another advantage in the use of a single elongated ablation electrode is the fact that a conventional, single-outlet standard ablation generator can be used for making the ablation energy available that is needed for the generation of an elongated linear lesion.

Preferred embodiments of the ablation catheter according to the invention are specified in the sub-claims. Further features, details and advantages of the invention will become apparent from the ensuing description of exemplary embodiments of the invention, taken in conjunction with the drawings.

BRIEF DESCRIPTION OF THE DRAWING

FIGS. 6A–C are radial sections through the distal end on the line VI—VI of FIG. 5 in successive steps of production;

DESCRIPTION OF THE PREFERRED EMBODIMENTS

Figure 1:
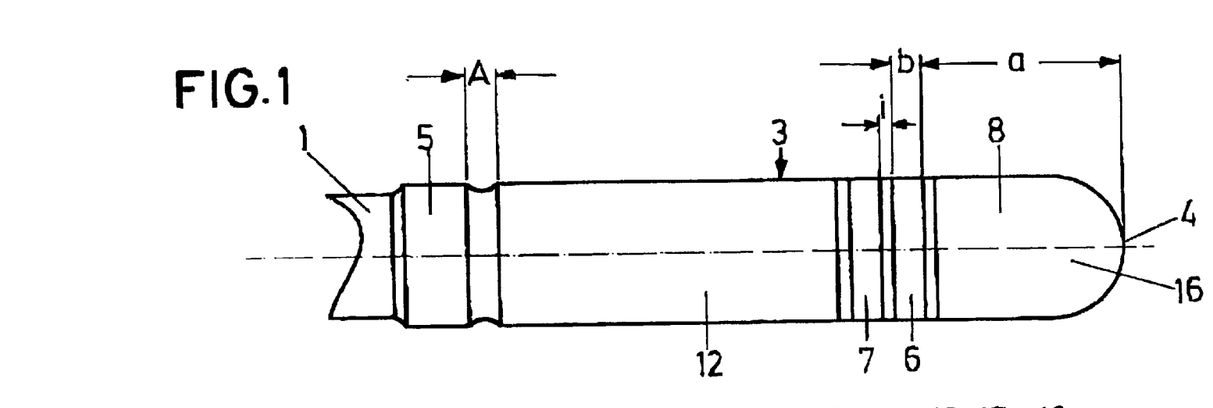
FIG. 1 is a lateral view of the distal end of a first embodiment of an ablation catheter.

The fundamental structure of an ablation catheter is to be explained on the basis of FIG. 1. An elongated catheter body 1 of circular cross-sectional shape is provided, which is illustrated only rudimentarily in FIG. 1 and all the other drawings. It consists of a physiologically well-tolerated, flexible plastic hose, the diameter of which is in the range of 1 to 2 mm. On the proximal end (not shown) of the catheter body, provision is made for a customary handle with corresponding actuation elements for directional control during insertion of the catheter into the body.

The distal end 2 of the catheter body 1 is provided with an ablation electrode which is designated in its entirety by 3 and has an elongated cylindrical shape with a rounded tip. The characteristic dimensions for the length 1 of the ablation electrode 3 and the diameter d are 1=10 mm and d=2.3 mm.

Approximately in the middle part of three equal parts of the ablation electrode 3, provision is made for two narrow annular sensing electrodes 6, 7 embedded in the jacket 8 of the ablation electrode 3. The two sensing electrodes 6, 7 are insulated from each other and also from the ablation electrode 3 by means of an insulating ring body 9. The insulating ring body 9 comprises two housing grooves 10, 11 which encircle the periphery of the insulating ring body 9 and the depth of which corresponds to the ring thickness of the sensing electrodes 6, 7. In this regard, the externally visible surfaces of the ablation electrode 3, the sensing electrodes 6, 7 and the insulating ring body 9 are in alignment.

The distal sensing electrode 6 has a distance a of approximately 3 mm from the tip 4. The insulating distance i between the sensing electrodes 6, 7 and towards the ablation electrode 9—as it is produced by the insulating ring body 9—is approximately 0.2 mm. The width b of the sensing electrodes 6, 7 is 0.5 mm.

Seen in the proximal direction, an annular auxiliary sensing electrode 5 is disposed before the ablation electrode 3; it is insulated and placed on the catheter body 1 at an axial distance A of approximately 0.5 mm from the ablation electrode 3. The sensing electrode 5 serves for scanning bipolar sewing signals not only between the sensing electrodes 6 and 7, but also between the electrodes 6 and 5 or 7 and 5 as required.

Figure 2:
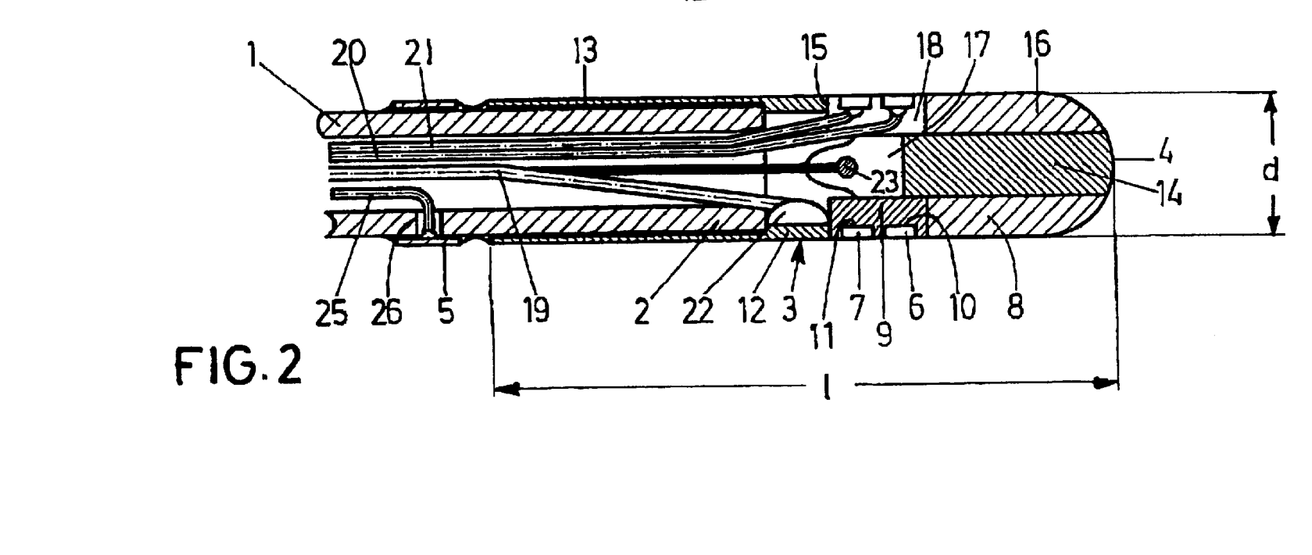
FIG. 2 is a longitudinal section through the ablation catheter according to FIG. 1.

As seen in FIG. 2, the ablation electrode 3, in the first embodiment shown, is formed by a substantially sleeve-type base member 12 turned towards the proximal direction and pushed on the distal end 2 of the catheter body 1. Fixing is effected by a suitable glued joint 13 between the catheter body 1 and the base member 12. In the distal direction, the base member 12 possesses a peg-shaped prolongation in the form of a shank 14, the outside diameter of which substantially corresponding to the inside diameter of the opening of the insulating ring body 9. Thus, the insulating ring body 9 can be pushed on the shank 14 from the distal end until it bears against the encircling annular shoulder 15 of the base member 12 of the ablation electrode 3. Then an end cap 16 of the ablation electrode 3 is pushed on the shank 14, which consists of the same material as the base member 12—namely a medical platinum iridium alloy. In the position of assembly seen in FIG. 2, the end cap 16 and the shank 14 of the base member 12 are tightly joined to each other at the tip 4 by laser welding.

As further seen in FIG. 2, the fitting portion of the shank 14 and the annular shoulder 15 as well as the insulating ring body 9 are provided with a flat, narrow slotted recess 17, 18, which coincides with the plane of the drawing in FIG. 2. The insulated connecting lines 19, 20, 21 for the ablation electrode 3 and the two sensing electrodes 6, 7 are led through these recesses 17 or 17 and 18, respectively. Fixing the cores (not shown) of the connecting lines 19, 20, 21 to the corresponding electrodes 3, 6, 7 is effected by respective soldering points 22. Finally, the auxiliary sensing electrode 5 is contacted via a connecting line 25. This connecting line 25 is guided outwards via an opening 26 in the catheter body 1.

Figure 3:
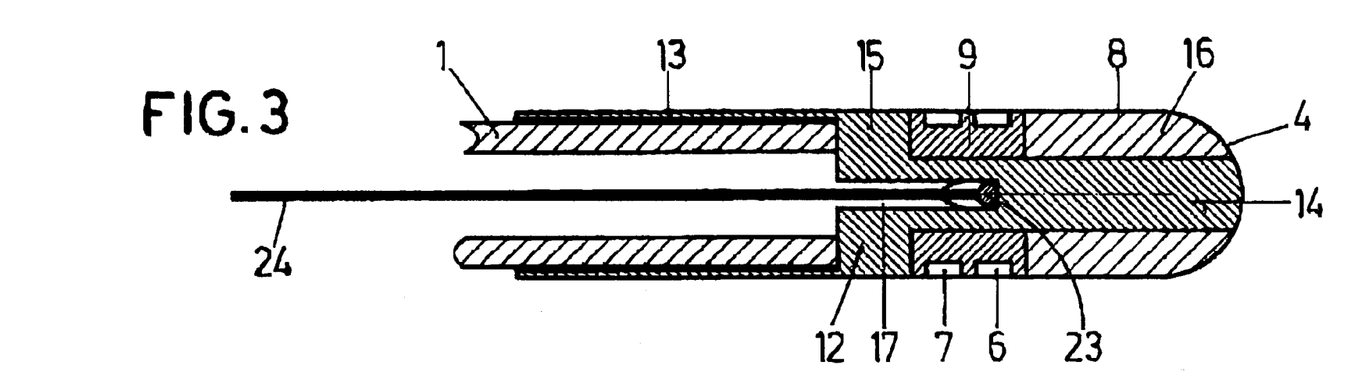
FIGS. 3 and 4 are two longitudinal axial sections, rotated by 90° relative to each other, through the distal end of a second embodiment of an ablation catheter.
Figure 4:
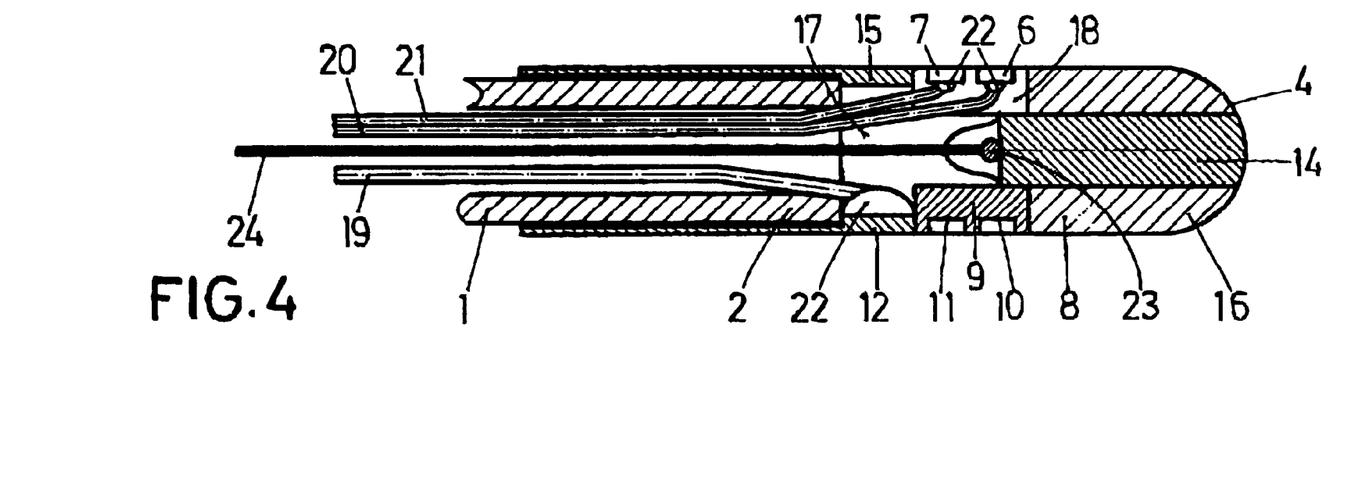

The embodiment of an ablation catheter seen in FIGS. 3 and 4 corresponds to the embodiment according to FIGS. 1 and 2 as regards the design of the ablation electrode 3 with sensing electrodes 6, 7. The only difference resides in the missing auxiliary sensing electrode 5. In this regard, a renewed explanation of the ablation electrode 3 illustrated in FIGS. 3 and 4 is not necessary, identical components have identical reference numerals. Attention is however drawn to FIG. 3, from which the position and shape of the recess 17 in the base member 12 becomes especially distinct by a comparison with FIG. 4 or FIG. 2.

As regards the embodiments according to FIGS. 1 to 4, it can be said that mounting the sensing electrodes 6, 7 in the housing grooves 10, 11 of the one-piece insulating ring body 9 may take place by analogy to the way of mounting specified below for the embodiment according to FIGS. 5 and 6.

Figure 5:
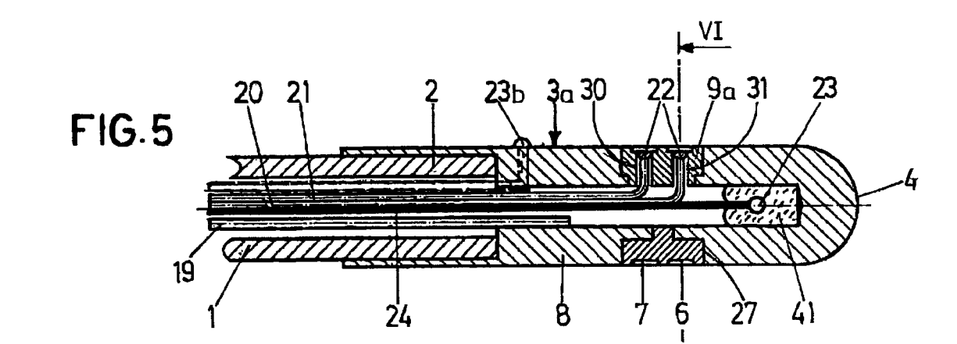
FIG. 5 is a longitudinal axial section through the distal end of a third embodiment of an ablation catheter.
Figure 6:
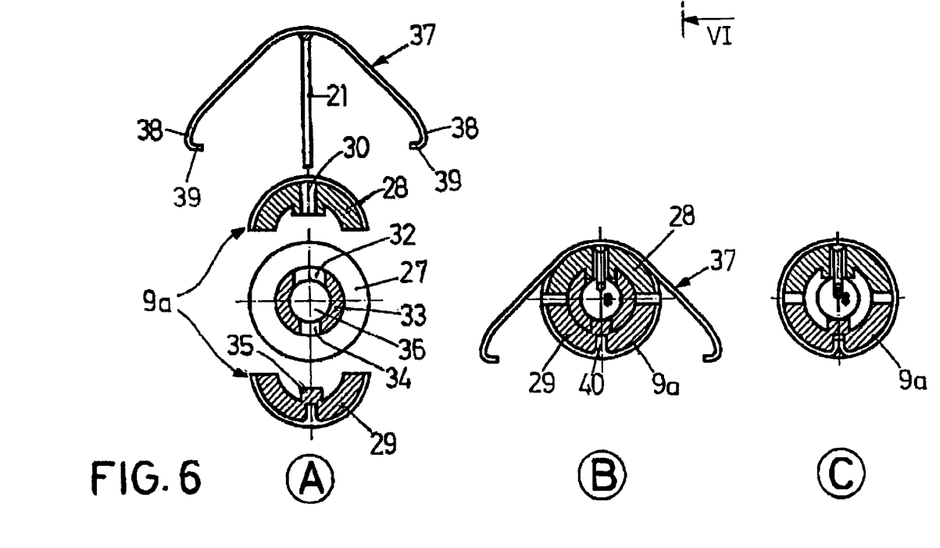

In the mentioned embodiment according to FIGS. 5 and 6, a one-piece ablation electrode 3a is placed on the catheter body 1, having an outer contour that is identical with FIGS. 1 to 4. Approximately centrically, the ablation electrode 3a has a deep annular groove 27 which serves to accommodate the insulating ring body 9a. This ring body 9a is divided into two members 28, 29 along the central longitudinal plane and can thus be inserted in the annular groove 27 from opposite sides as becomes apparent from FIG. 6A in combination with 6B. The member 28 of the insulating body 9a, which is the upper member in FIG. 5 and 6A, is provided with two radial orifices 30, 31 which are prolonged radially inwards, leading through a corresponding radial passage 32 in the core ring 33 on the bottom of the annular groove 27. On the opposite side, the core ring 33 is provided with a centering opening 34 which, as a safeguard against rotation, cooperates with a projection 35 which projects inwards from the second member 29 of the insulating ring body. A longitudinal hole 36 into which the orifices 30, 31 open is provided centrally in the ablation electrode 3a.

As seen in FIG. 6, the two sensing electrodes 6, 7 are made from a correspondingly preformed bent component 37, which is V-shaped in a side view and on which the respective connecting line 20 or 21 (FIG. 6A) is soldered once it has been threaded through the catheter body 1. Then the bent component 37 is placed on the members 28, 29 of the insulating ring body 9a which are inserted in the annular groove 27 (FIG. 6B) and then the free ends 38 of the two legs of the bent component 37 are bent around the insulating ring body 9a in the circumferential direction for the bent component 37 to rest in the corresponding housing grooves 10 and 11 of the insulating ring body 9a. Two short end pieces 39 are provided on the free ends 38 of the bent component 37; they are bent inwards and reach into a correspondingly shaped slit 40 in the lower member 29 of the insulating ring body 9a when the bent component 37 is folded down (FIG. 6C). In this position the two end pieces 39 can be joined by laser welding, whereby the sensing electrodes 6 and 7 are secured on the insulating ring body 9a and the insulating ring body 9a is simultaneously fixed on the ablation electrode 3a.

As seen in FIG. 5, a thermoelement 23 with a connecting line 24 is fixed on the distal end of the longitudinal hole 36 by means of a drop of glue 41. Further, a thermoelement 23b is illustrated by dashes in FIG. 5; it is seated on the outside of the ablation electrode 3a and may be used by alternative or in addition to the thermoelement 23. This further thermoelement 23b can be put in circuit and mounted on the ablation electrode so that it serves as an additional electric sensing electrode.

In the embodiment seen in FIG. 7, provision is again made for an ablation electrode 3b of several parts, in which the base member 12a does not comprise a shank that is directly molded on, but a narrower pipe member 42 of a PtIr alloy. Placed on this pipe member 42 is the insulating ring body 9b in the form of several individual partial rings 43, 44, 45 which, by means of peripherally encircling annular shoulders 46, form the grooves 10, 11 housing the two sensing electrodes 6, 7. The parting planes between the partial rings 43, 44, 45 lie on the center plane of the housing grooves 10, 11.

Figure 7:
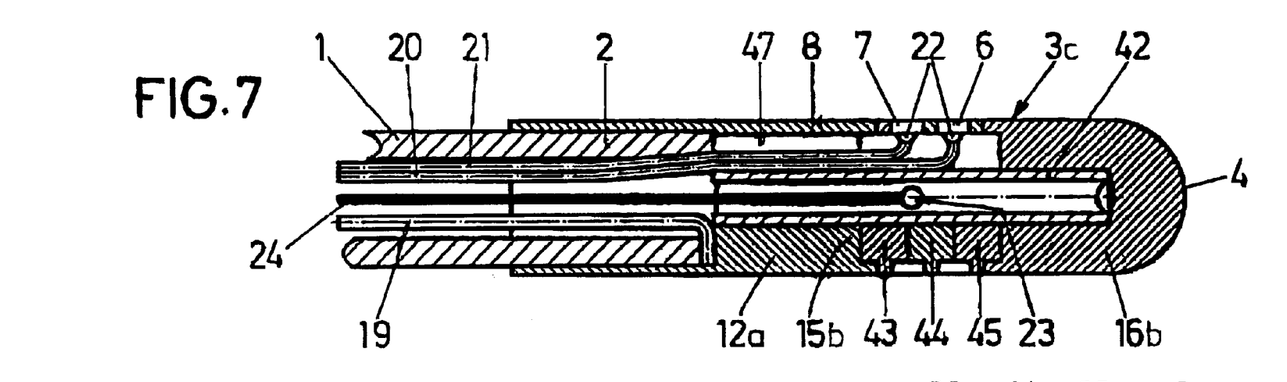
FIGS. 7 and 8 are longitudinal axial sections of the distal end of a fourth and fifth embodiment of ablation catheters.

For the assembly of the ablation electrode 3b, the partial ring 43, the sensing electrode 6, the partial ring 44, the sensing electrode 7 and finally the partial ring 45 are threaded successively on the pipe member 42. Then the end cap 16b is placed on the pipe member 42 and compressed. Optionally the individual parts may also be mounted by undersize and press-fit, after which they need not be compressed.

Contacting the individual electrodes 3b, 6, 7 takes place via corresponding connecting lines 19, 20, 21. The connecting lines 20, 21 for the sensing electrodes 6, 7 are guided in a longitudinal groove 47 radially outside and past the pipe member 42 towards the sensing electrodes 6, 7. The connecting line 19 for the ablation electrode 3b is led outwards between the distal end 2 of the catheter body 1 and the annular shoulder 15b of the base member 12a. Again provision is made for a thermoelement 23 which is fixed on the pipe member 42 approximately centrically of the length thereof.

Figure 8:
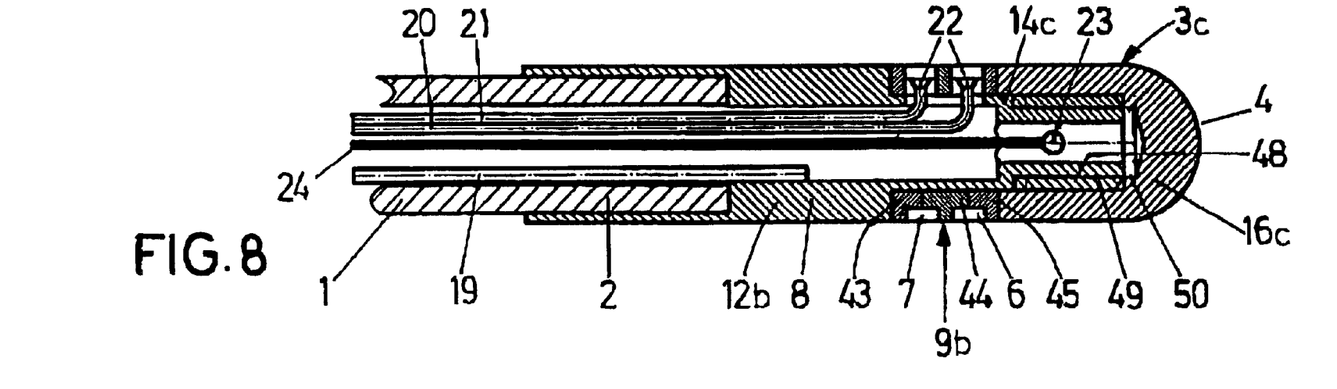

The embodiment of the ablation catheter seen in FIG. 8 comprises an ablation electrode 3b which is again divided into a base member 12b and an end cap 16c. A shank 14c is molded on the base member 12b, having an external thread 48. This thread 48 cooperates with an internal thread 49 of an internally threaded hole 50 which is provided in the end cap 16c. In this regard, the ablation electrode 3c may again be assembled by the partial rings 43, 44, 45 and the sensing electrodes 6, 7 being threaded on the shank 14c and by the end cap 16c being screwed on subsequently. The further components such as connecting lines 19, 20, 21 etc. correspond to the embodiments specified above.

Figure 9:
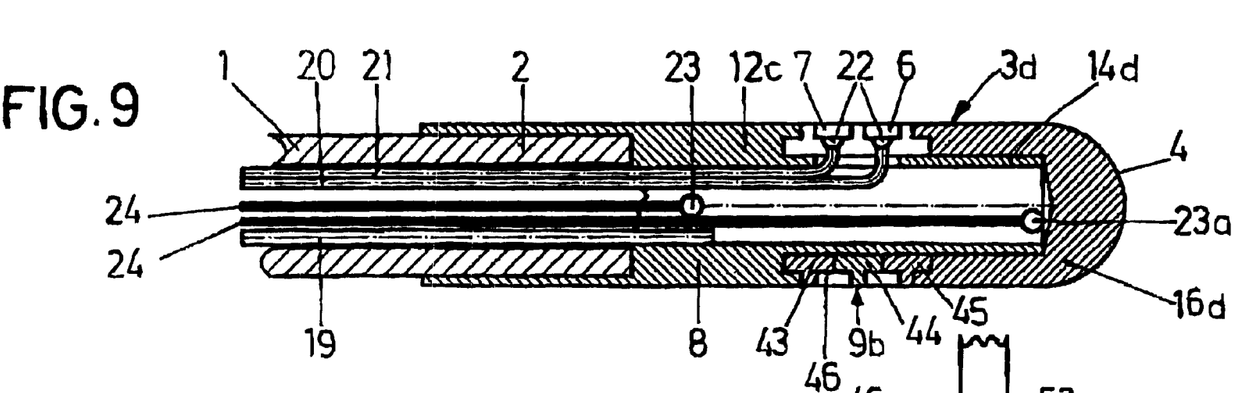
FIG. 9 is a longitudinal axial section through the distal end of a sixth embodiment of an ablation catheter.
Figure 10:
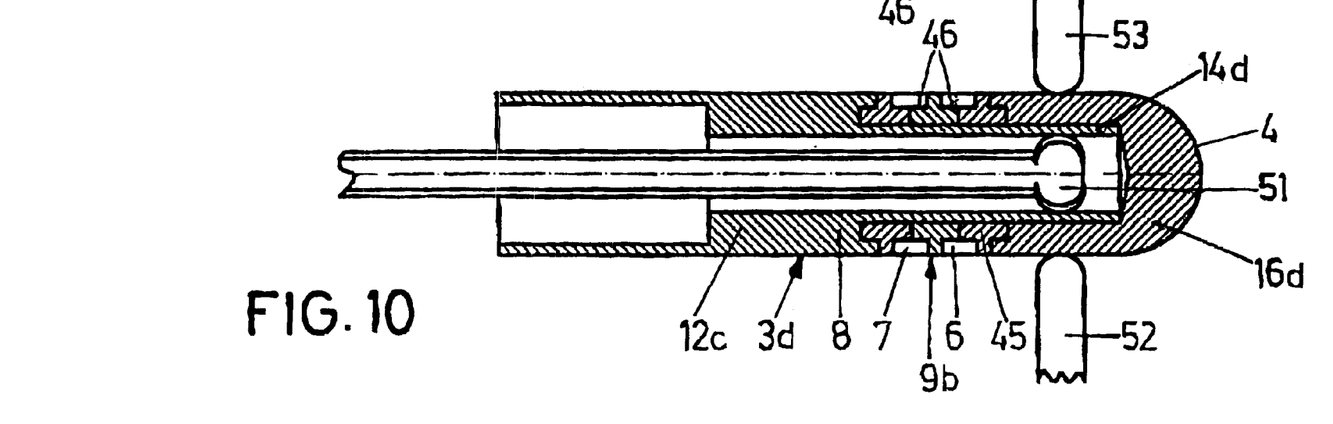
FIG. 10 is a longitudinal axial section through the distal end of the ablation catheter of FIG. 9 in an intermediate step of production.

The embodiment of the ablation electrode 3d seen in FIGS. 9 and 10 differs from that according to FIG. 8 only in that the shank 14d is smooth and the end cap 16d is pushed thereon and electric resistance welded. FIG. 10 illustrates a corresponding intermediate step of production with welding electrodes 51, 52, 53 attached between the end cap 16d and the passage 32d in the shank 14d.

As can further be seen from FIG. 9, this embodiment comprises two thermoelements 23, 23a with corresponding connecting lines 24, 24a. The thermoelements 23, 23a are disposed in the vicinity of the tip 4 and in the area of transition from the base member 12c to the catheter body 1.

Figure 11:
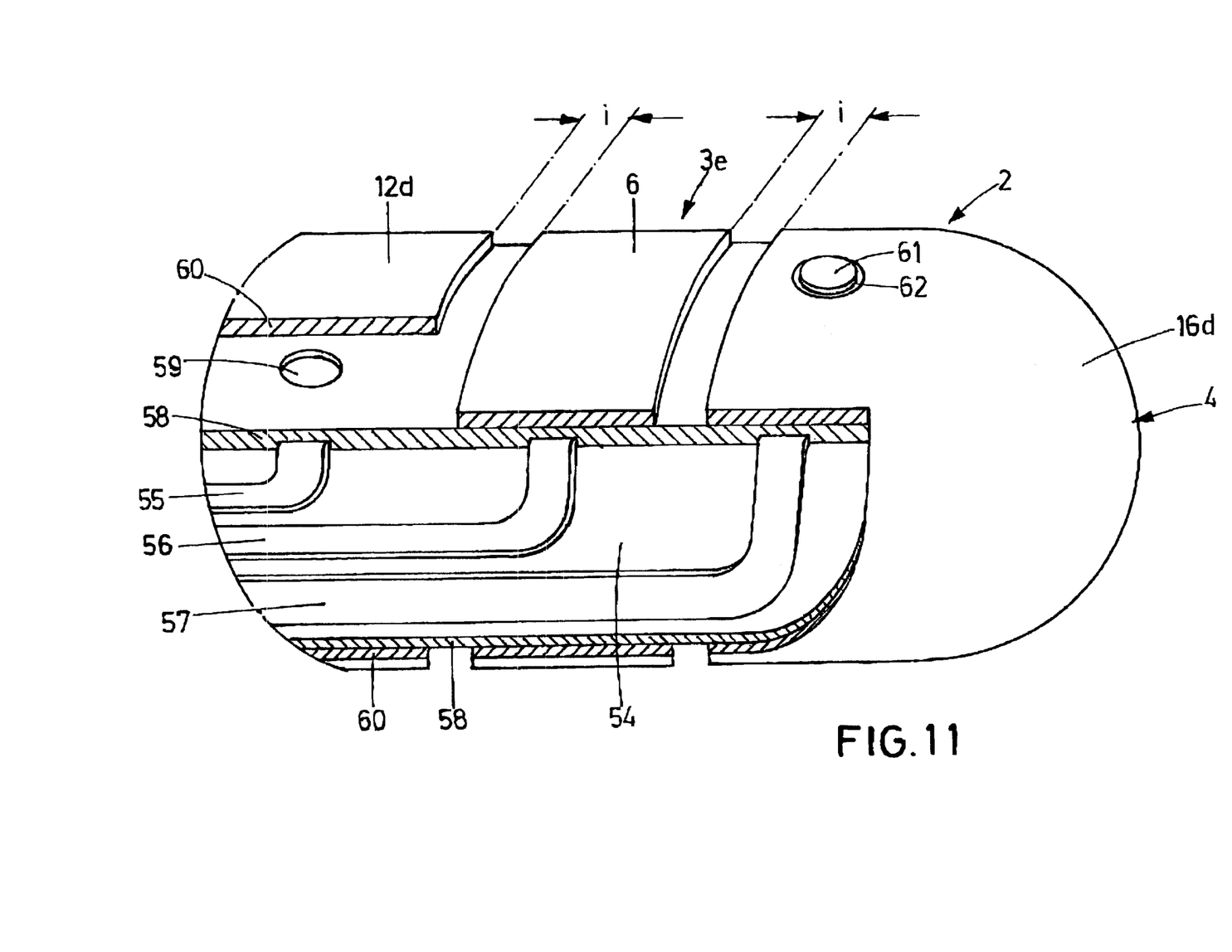
FIG. 11 is a perspective view, partly broken away, of the distal end of a seventh embodiment of an ablation catheter.

FIG. 11 shows another embodiment of an ablation catheter with a distal ablation electrode 3e which is produced on the basis of a three-dimensional structuring technology known in the field of manufacture of electronic components. On the one hand structuring technologies of this type are known in the form of so-called laser-selective methods.

Defined portions of a layer, which may be a conductor or an insulator, are exposed to laser abrasion, whereby corresponding conductive or insulating structures are produced on a substrate. On the other hand three-dimensional structuring technologies are also applicable on the basis of polymerization of electrically conductive or insulating pastes by means of locally irradiated laser energy. This technology is known as laser sintering.

The distal end 2 of the ablation electrode 3e comprises a substantially cylindrical main body 54 which constitutes the supporting core of the ablation electrode 3e and consists of ceramics or plastics and has dielectric properties. This main body 54 is of decisive importance for the geometry of the distal end 2, configuring in the so-called structural plane 0. For good order's sake it must be mentioned that of course the "plane" of the present embodiment arches in the shape of a cylinder jacket.

Electrically conductive strip conductors 55, 56, 57 are applied on the main body 54, serving for contacting the individual electrodes which still remain to be explained. These strip conductors are formed on the first structural plane of the layered structure.

Then an insulating layer 58 is applied on the main body 54, enclosing the strip conductors 55, 56, 57 and constituting the second structural plane of the electrode structure. This insulating layer 58 consists of a biocompatible material and may have openings where suitable, creating a possibility of contacting for the electrically conductive layers applied on the insulating layer 59 for the formation of the individual electrode components. This structured conductive layer, which is designated in its entirety by 60, is configured such that on the one hand the base member 12d of the ablation electrode 3e is formed from it, the electric contacting of which takes place via the opening 59 by the strip conductor 55. An annular sensing electrode 6 is positioned at an insulating distance i from the base member 12d and the end cap 16d which is also formed from a corresponding conductive layer; the sensing electrode 6 is electrically connected via openings (not shown) by the aid of the strip conductor 56.

A point shaped sensing electrode 61 is fitted into the end cap 16d of the ablation electrode 3e, having an insulating annular gap 62 towards the end cap 16d. Further point electrodes may be distributed along the circumference of the end cap 16d—not seen in the drawing—and, together with the point electrode 61, they can be electrically connected via the strip conductor 57. The strip conductor of the end cap 16d cannot be seen in FIG. 11.

The electrically conductive layer 60, which constitutes the third structural plane of the layered structure and from which the various electrodes are formed, is also made biocompatible in light of the fact that there is contact to the cardiac tissue.

In addition to the mentioned laser method of surface structuring of the ablation electrode 3e, use may also be made of a cathode ray coating method, employing a correspondingly designed mask.

In conclusion, attention is drawn to the fact that the three-dimensional structuring method of forming the electrode arrangement of the ablation catheter, which is explained on the basis of the embodiment according to FIG. 11, is applicable also in the case of differently configured and designed electrodes and is not linked to the sensing electrodes embedded in the ablation electrode.

For example, electrodes may be provided in an orthogonal array, detecting the direction of stimulus conduction; or there may be spaced electrodes, measuring the velocity of stimulus conduction or simply the electric signals of the heart at varying places in the myocardium.

What is claimed is:

1. An ablation catheter for the generation of linear lesions in the myocardium, comprising:

an elongated catheter body (1) with a proximal and a distal end (2);

a linear, substantially cylindrical ablation electrode (3, 3a, 3b, 3c, 3d, 3e) on the distal end (2) of the catheter body (1); and at least one sensing electrode (6, 7, 61) embedded in a lateral surface (8) of the ablation electrode (3, 3a, 3b, 3c, 3d, 3e) and insulated therefrom so that the electrically active surface of the ablation electrode extends both distal and proximal of the at least one sensing electrode (6, 7, 61), which is a narrow ring electrode.

2. An ablation catheter according to claim 1, wherein at least two sensing electrodes (6, 7, 61) are provided on the ablation electrode (3, 3a, 3b, 3c, 3d, 3e), which are spaced and insulated from each other.

3. An ablation catheter according to claim 2, wherein a distance (A) between both said sensing electrodes (6, 7) ranges between 0.1 mm and 0.4 mm and is preferably approximately 0.2 mm, and a width (b) of the sensing electrodes (6, 7) ranges between 0.2 mm and 0.8 mm and is preferably approximately 0.5 mm.

4. An ablation catheter according to claim 1, wherein the at least one sensing electrode (6, 7) is located in an insulating ring body (9, 9y, 9b), which is housed in an annular groove (27) the circles the jacket of the ablation electrode (3, 3a, 3b, 3c, 3d).

5. An ablation catheter according to claim 4, wherein the ablation electrode (3a) forms a single piece, with the insulating ring body (9a) that is seated in the annular groove (27) comprising two pieces (28, 29) which are inserted into the annular groove (27) from opposite sides; and with the at least one sensing electrode (6, 7) being inserted as a bent component (37) into a housing groove (10, 11) of the insulating ring body (9a) and bent around a circumference of the insulating ring body (9a).

6. An ablation catheter according to claim 5, wherein the bent ends (39) of the at least one sensing electrode (6, 7) are welded together.

7. An ablation catheter according to claim 4, wherein the ablation electrode (3, 3b, 3c, 3d) comprises a base member (12, 12b, 12c, 12d) which is turned towards a proximal direction and an end cap (16, 16b, 16c, 16d) which constitutes a distal tip (4) of the ablation electrode (3, 3b, 3c, 3d), with the at least one sensing electrode (6, 7) and the insulating ring body (9, 9b, 9c, 9d), which is composed of several partial rings (43, 44, 45), being threaded on a shank (14, 14b, 14c, 14d) which is disposed between the base member (12, 12b, 12c, 12d) and the end cap (16, 16b, 16c, 16d).

8. An ablation catheter according to claim 7, wherein the shank (14, 14b, 14c, 14d) forms a single piece with the base member (12, 12b, 12c, 12d) of the ablation electrode (3, 3b, 3c, 3d).

9. An ablation catheter according to claim 1, the ablation electrode (3, 3a, 3b, 3c, 3d) is provided inside with at least one thermoelement (23, 23a) monitoring the temperature of the ablation electrode (3, 3a, 3b, 3c, 3d).

10. An ablation catheter according to claim 1, wherein a thermoelement (23b) is disposed on an outside of the ablation electrode (3a).

11. An ablation catheter according to claim 10, wherein the outer thermoelement (23b) simultaneously works as a sensing electrode.

12. An ablation catheter according to claim 1, wherein the ablation electrode (3e) and the sensing electrodes (6, 61) are formed in layers on a main body (54) by three-dimensional structuring.

13. An ablation catheter according to claim 1, wherein several electrically coupled, substantially point shaped sensing electrodes (61) are distributed along a circumference of the ablation electrode (3e).

* * * * *